(12) United States Patent
Mikami

(10) Patent No.: US 9,612,108 B2
(45) Date of Patent: Apr. 4, 2017

(54) MEASUREMENT APPARATUS AND MEASUREMENT METHOD

(71) Applicant: KABUSHIKI KAISHA TOSHIBA, Minato-ku (JP)

(72) Inventor: Toru Mikami, Yokkaichi (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 55 days.

(21) Appl. No.: 14/657,209

(22) Filed: Mar. 13, 2015

(65) Prior Publication Data

US 2016/0139034 A1 May 19, 2016

Related U.S. Application Data

(60) Provisional application No. 62/079,897, filed on Nov. 14, 2014.

(51) Int. Cl.
*G01B 11/16* (2006.01)
*G01B 11/02* (2006.01)
(Continued)

(52) U.S. Cl.
CPC ............ *G01B 11/02* (2013.01); *G01J 3/0264* (2013.01); *G01J 3/4412* (2013.01);
(Continued)

(58) Field of Classification Search
CPC .. G01N 21/211; G01N 25/4846; G01N 11/00; G01N 15/088; G01N 2021/95615;
(Continued)

(56) References Cited

U.S. PATENT DOCUMENTS 5,900,633 A * 5/1999 Solomon ............ G01B 11/0625
250/339.08
2002/0192577 A1 12/2002 Fay et al.
(Continued)

FOREIGN PATENT DOCUMENTS

JP 2003-68639 3/2003
JP 2005-140554 6/2005
(Continued)

*Primary Examiner* — Michael P Stafira
(74) *Attorney, Agent, or Firm* — Oblon, McClelland, Maier & Neustadt, L.L.P.

(57) ABSTRACT

In accordance with an embodiment, a measurement apparatus includes a library creation unit, a spectral profile acquiring unit, and a measurement unit. The library creation unit creates a library in which a layer stack model is matched to a theoretical profile regarding a pattern of stacked layers. The spectral profile acquiring unit acquires an actual measured profile by applying light to a measurement target pattern obtained when the pattern is actually created. The measurement unit measures the sectional shape of the measurement target pattern by performing fitting of the theoretical profile to the actual measured profile. The layer stack model is created by calculating a feature value that reflects the intensity of reflected light from an interface for each of the layers, determining a priority order of analysis from the feature value, and sequentially performing fitting of the theoretical profile to the measured profile in the determined priority order.

6 Claims, 10 Drawing Sheets

(51) Int. Cl.
- *G01J 3/44* (2006.01)
- *G01J 3/02* (2006.01)
- *G01N 21/95* (2006.01)
- *G01N 21/956* (2006.01)
- *G01J 3/28* (2006.01)

(52) U.S. Cl.
CPC ... *G01N 21/9501* (2013.01); *G01N 21/95607* (2013.01); *G01J 2003/284* (2013.01); *G01N 2021/95615* (2013.01)

(58) Field of Classification Search
CPC ....... G01N 2035/00237; G01N 21/255; G01N 21/9501; G01N 21/95607; G01N 21/95623; G01N 2291/0256; G01N 29/036; G01N 31/10
See application file for complete search history.

(56) References Cited

U.S. PATENT DOCUMENTS

| | | |
|---|---|---|
| 2003/0223066 A1 | 12/2003 | Lee et al. |
| 2004/0260420 A1* | 12/2004 | Ohno ................... G01N 21/211 700/121 |
| 2005/0151980 A1 | 7/2005 | Mikami et al. |
| 2006/0117293 A1 | 6/2006 | Smith et al. |
| 2007/0153274 A1 | 7/2007 | Van Der Aa et al. |
| 2007/0153275 A1 | 7/2007 | Aa et al. |
| 2008/0050676 A1* | 2/2008 | Hoshino ................ B82Y 10/00 430/296 |
| 2009/0233195 A1 | 9/2009 | Miyashita |
| 2010/0046006 A1* | 2/2010 | Mitsui ................... G01B 11/24 356/604 |
| 2013/0208973 A1 | 8/2013 | Brill |

FOREIGN PATENT DOCUMENTS

| | | |
|---|---|---|
| JP | 2006-157023 | 6/2006 |
| JP | 2007-201443 | 8/2007 |
| JP | 2008-111911 | 5/2008 |
| JP | 2009-22640 A | 2/2009 |
| JP | 2009-58516 | 3/2009 |
| JP | 2009-117691 | 5/2009 |
| JP | 2009-222640 | 10/2009 |
| JP | 2010-204117 | 9/2010 |
| JP | 2013-531794 | 8/2013 |
| JP | 2014-36147 | 2/2014 |
| WO | WO 2008/038751 A1 | 4/2008 |
| WO | WO 2011/158239 A1 | 12/2011 |

* cited by examiner

REFLECTION (Top)

| | AngleOfLight(Top) | ExtinctionByFilm(D) | Reflectivity(Top) | | Transmittivity(Top) | |
|---|---|---|---|---|---|---|
| | | | P | S | P | S |
| Air | 20.0 | | | | | |
| SiN | 9.8 | 0.4705 | 0.3121 | -0.3542 | 0.6561 | 0.6458 |
| Poly | 2.1 | 0.0001 | 0.6412 | -0.6494 | 0.3538 | 0.3506 |
| Si | 0.4 | | 0.6494 | -0.6498 | 0.3504 | 0.3502 |

FIG. 6A

REFLECTION (Wall)

| | AngleOfLight(Wall) | Reflectivity(Wall) | | P+S |
|---|---|---|---|---|
| | | P | S | |
| Air | 70.0 | | | |
| SiN | 28.0 | -0.1268 | -0.6754 | 0.687231 |
| Poly | 11.7 | 0.2367 | -0.8600 | 0.891945 |
| Si | 11.5 | 0.2433 | -0.8619 | 0.895626 |

FIG. 6B

MEASUREMENT APPARATUS AND MEASUREMENT METHOD

CROSS REFERENCE TO RELATED APPLICATIONS

This application is based upon and claims the benefit of U.S. provisional Application No. 62/079,897, filed on Nov. 14, 2014, the entire contents of which are incorporated herein by reference.

FIELD

Embodiments described herein relate generally to a measurement apparatus and a measurement method.

BACKGROUND

In addition to manufacturing processes such as a lithographic process, a film formation process, and an etching process, manufacture of a semiconductor device requires a measurement process of a micropattern created by the above processes for the improvement of yield.

Recently, to meet the needs for higher performance and higher functions in devices, the size of a pattern has been made minuter, and its two-dimensional and three-dimensional shapes have also been increasingly complex. In order to evaluate the pattern having the complex shapes, it is necessary to measure the sectional shape of the pattern, compared to conventional critical dimension (CD) measurement that only measures the CD of a particular part of the pattern section.

The use of scatterometry that utilizes light has recently been on the increase. The scatterometry is a technique in which light is applied to a measurement target pattern, and a pattern sectional shape corresponding to the spectral profile of the reflected light is estimated by referring to a library which depends on a pattern sectional shape previously constructed by a numerical calculation.

The advantages of the scatterometry include being a nondestructive measurement and being able to measure not only the CD but also, for example, the height and sidewall angle of the pattern.

On the other hand, the scatterometry requires the previous construction of the library, so that know-how is needed to construct a layer stack model from, for example, a sectional photograph of the pattern. In particular, a good library needs to be created to obtain accurate measurement results, for which considerable cost (labor and time for a skilled engineer) has been required.

BRIEF DESCRIPTION OF THE DRAWINGS

In the accompanying drawings:

FIG. 6A shows an example of reflectivities and transmittivities found with regard to lights generated from the upper surface (top surface) of the pattern shown in FIG. 4;

FIG. 6B shows an example of reflectivities found with regard to light generated from the side surface of the pattern shown in FIG. 4;

DETAILED DESCRIPTION

In accordance with an embodiment, a measurement apparatus includes a library creation unit, a spectral profile acquiring unit, and a measurement unit. The library creation unit creates a library in which a layer stack model is matched to a theoretical profile regarding a pattern constituted by a plurality of stacked layers, the theoretical profile being obtained by calculating a spectral profile expected when light is applied to the layer stack model. The spectral profile acquiring unit acquires an actual measured profile by applying light to a measurement target pattern obtained when the pattern is actually created. The measurement unit measures the sectional shape of the measurement target pattern by performing fitting of the theoretical profile in the library to the actual measured profile. The library creation unit creates the layer stack model by calculating a feature value that reflects the intensity of reflected light from an interface for each of the layers, determining a priority order of analysis from the feature value, and sequentially performing fitting of the theoretical profile to the measured profile in the determined priority order.

Embodiments will now be explained with reference to the accompanying drawings. Like components are provided with like reference signs throughout the drawings and repeated descriptions thereof are appropriately omitted. It is to be noted that the accompanying drawings illustrate the invention and assist in the understanding of the illustration and that the shapes, dimensions, and ratios and so on in each of the drawings may be different in some parts from those in an actual apparatus.

Although a micropattern created in manufacturing processes of a semiconductor device such as a lithographic process and an etching process is measured in the case described by way of example in the following embodiment, the present invention is not limited to this case. It is to be noted that the present invention is applicable to pattern evaluations in general in various other industrial fields.

In the present application, a shape model of the whole pattern constituted by stacked layers is defined as "a stack layer model" to discriminate it from a shape model of each layer.

(1) Measurement Apparatus

Figure 1:
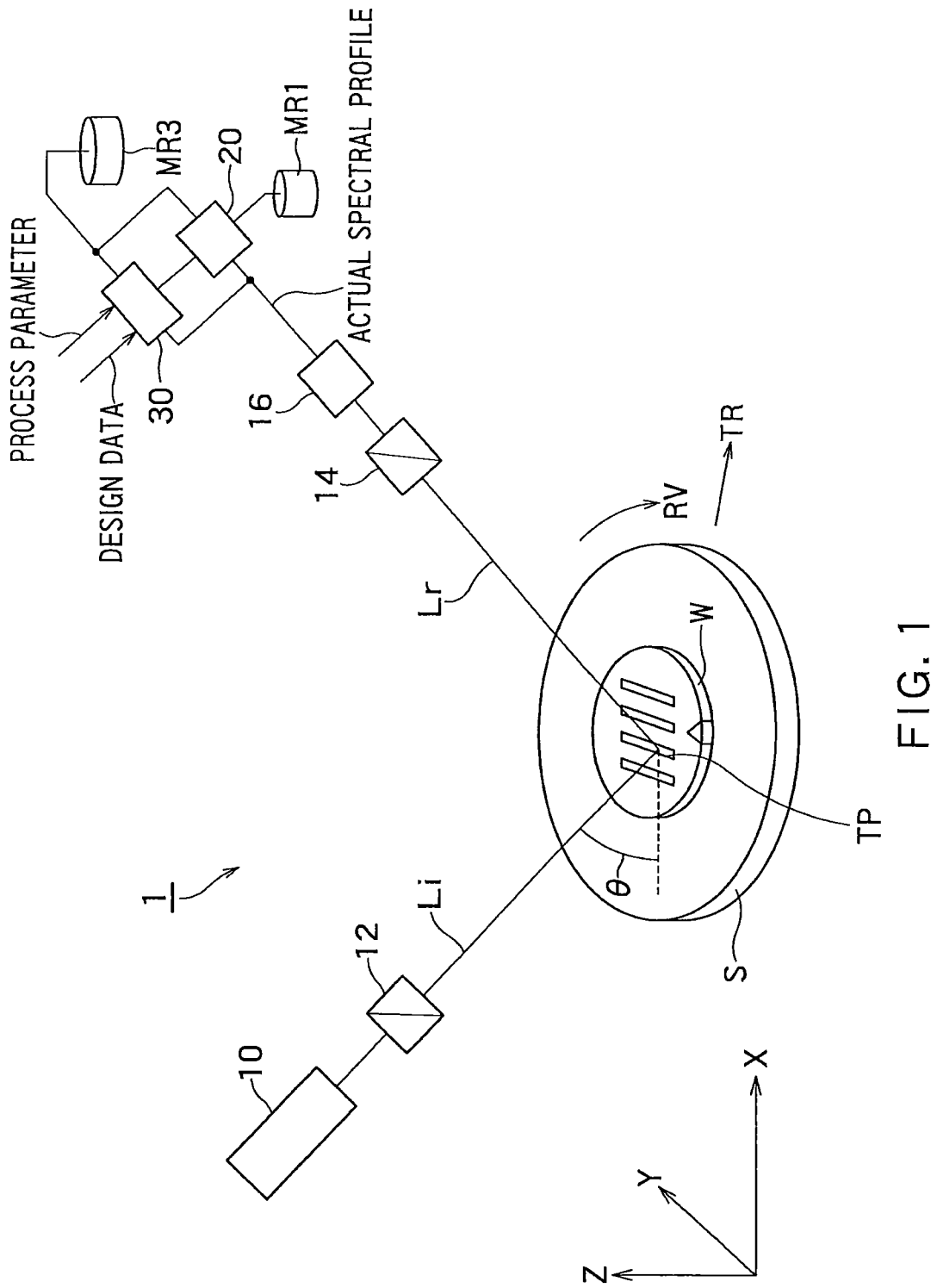
FIG. 1 is an example of a block diagram showing the general configuration of a measurement apparatus according to one embodiment.

FIG. 1 is an example of a block diagram showing the general configuration of a measurement apparatus according to one embodiment. A measurement apparatus 1 according to the present embodiment includes a light source 10, a polarizer 12, a stage S, an analyzer 14, an array detector 16, a computer 20, a library creation unit 30, and storage devices MR1 and MR3.

The light source 10 emits white light Li. The stage S moves a wafer W by rotary motion (RV direction) and translation motion (TR direction). A pattern TP as a measurement target obtained by actually creating a given pattern on the wafer W is created on the surface of the wafer W. Process parameters are set in such a manner that a desired shape is obtained for the creation of the pattern TP, and the set process parameters are used to create the pattern TP on the surface of the wafer W. The process parameters not only include dose and focus but also include parameters such as an exposure wavelength, a numerical aperture (NA) of a lens of an exposure unit, the illumination shape (σ, ε) of the exposure unit, the phase and transmittivity of a mask, and development and a resist process.

The array detector 16 includes a spectroscope, and outputs an actual spectral profile (hereinafter referred to as a "measurement profile" when proper) of the pattern TP.

In the present embodiment, the light source 10, the polarizer 12, the stage S, the analyzer 14, and the detector 16 correspond to, for example, a spectral profile acquiring unit.

The computer 20 is connected to the library creation unit 30 and the storage devices MR1 and MR3. The computer 20 reads, from the storage device MR1, a recipe file in which later-described processing procedures of pattern measurement are described. The computer 20 causes the library creation unit 30 to create a later-described library, and uses the created library to measure the measurement target pattern TP.

The storage device MR1 has a plurality of storage areas. The storage device MR1 stores the above-mentioned recipe file, and also stores the measured profile of the pattern TP sent from the detector 16 to the computer 20.

The storage device MR1 is not only connected to the computer 20 but also connected to the library creation unit 30. The library creation unit 30 is connected to the storage device MR3.

The library creation unit 30 creates a library by the later-described processing procedures in response to a control signal from the computer 20, and stores the library in the storage device MR3.

Figure 2:
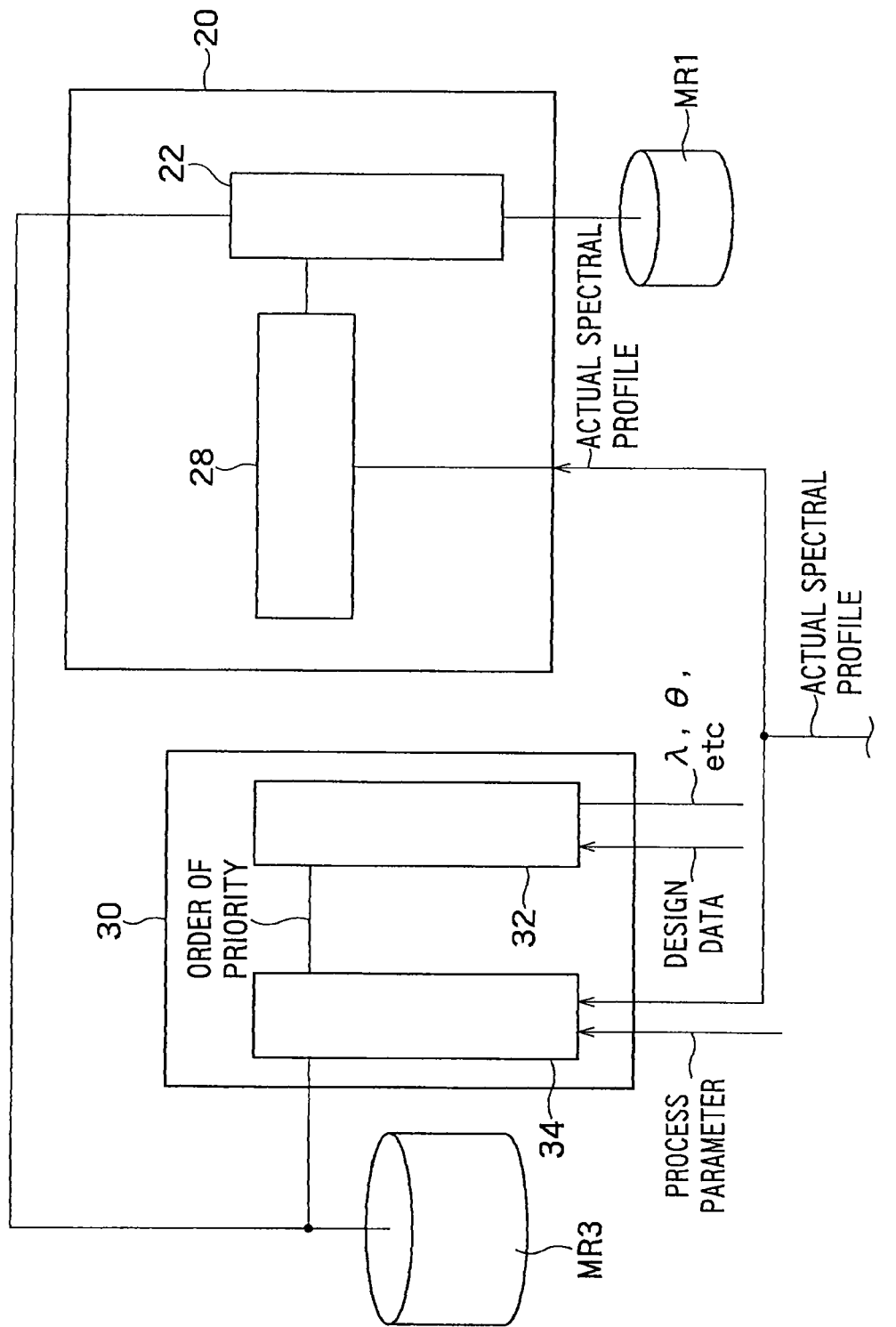
FIG. 2 is an example of a block diagram showing more detailed configurations of a computer and a library creation unit included in the pattern measurement apparatus shown in FIG. 1.

FIG. 2 is an example of a block diagram showing more detailed configurations of the computer 20 and the library creation unit 30 included in the pattern measurement apparatus 1 shown in FIG. 1.

As shown in FIG. 2, the computer 20 includes a control unit 22 and a pattern sectional shape measurement unit 28.

The control unit 22 is not only connected to the pattern sectional shape measurement unit 28 but also connected to the storage devices MR1 and MR3. The control unit 22 supplies control signals to the pattern sectional shape measurement unit 28 and the storage devices MR1 and MR3.

The pattern sectional shape measurement unit 28 is connected to the detector 16. In response to the input of an actual spectral profile of the pattern TP as a measurement target from the detector 16, the pattern sectional shape measurement unit 28 performs fitting of a theoretical profile in the library to the actual spectral profile by referring to the library stored in the storage device MR3 via the control unit 22, and thus generates an optimum pattern sectional shape, and then measures the pattern TP from the obtained sectional shape. In the present embodiment, the pattern sectional shape measurement unit 28 corresponds to, for example, a measurement unit.

The library creation unit 30 includes an analytic order determination unit 32 and a layer stack model determination unit 34.

In response to, for example, the input of a wavelength λ of the white light Li, an angle of incidence θ to the pattern TP, design data regarding the pattern TP, and refractive indexes of the layers constituting the pattern TP from the light source 10 via an unshown input unit, the analytic order determination unit 32 calculates a feature value S that reflects the intensity of reflected light from the interface for each layer, determines a priority order of analysis from the obtained feature value S, and sends the priority order to the layer stack model determination unit 34.

The layer stack model determination unit 34 sequentially determines shape models of the layers in accordance with the priority order provided from the analytic order determination unit 32, and thereby determines a layer stack model of the pattern TP. In determining each shape model, the layer stack model determination unit 34 allocates shape parameters in accordance with expected process variation to generate a candidate shape model (hereinafter referred to as a "candidate model") in response to the input of the process parameters via the unshown input unit, and calculates a theoretical profile of the spectral profile by a simulation for each candidate model. The layer stack model determination unit 34 then takes the actual spectral profile of the pattern TP out of the storage device MR1 via the computer 20, performs fitting of the calculated theoretical profile to the measured profile, and thereby selects the most suitable candidate model and specifies this candidate model as the shape model of the layer.

More specific operation of the pattern measurement apparatus 1 according to the present embodiment is described with reference to FIG. 3 to FIG. 8B.

Figure 3:
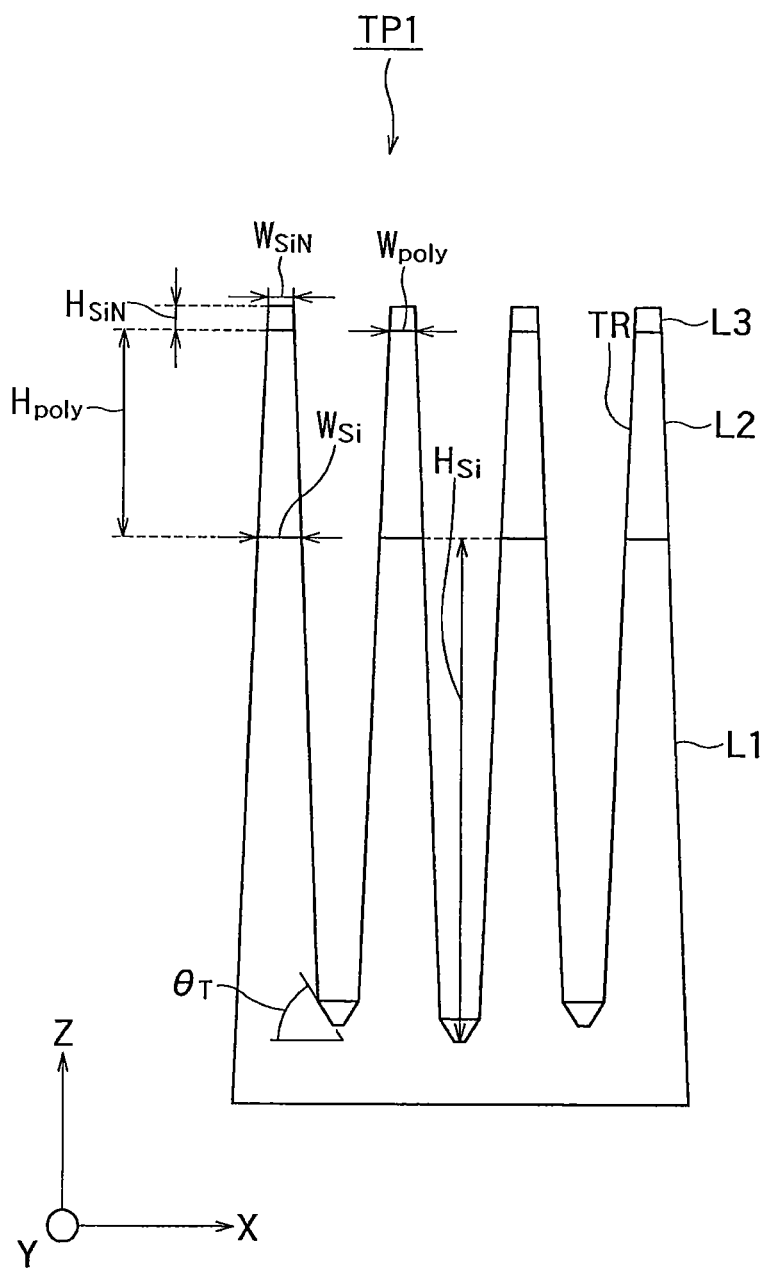
FIG. 3 is an example of a partial sectional view showing an example of a pattern TP which is a measurement target.

FIG. 3 is an example of a partial sectional view showing an example of the pattern TP which is the measurement target. A pattern TP1 shown in FIG. 3 includes a silicon layer (Si) L1, a polysilicon (PolySi) layer L2, and a silicon nitride (SiN) layer L3 that are stacked in this order, and is provided with trenches TR at predetermined intervals in the X-direction. The (X-direction) widths of the top surfaces of the layers L1 to L3 are $W_{Si}$, $W_{Poly}$, and $W_{SiN}$. The heights (depths when seen from the front side of e sample) of the layers L1 to L3 are $H_{Si}$, $H_{Poly}$, and $H_{SiN}$. The taper angle of the layer L1 is $\theta_T$.

Before measurement, necessary data is input to the analytic order determination unit 32 of the library creation unit 30 from the unshown input unit. More specifically, for example, the wavelength λ of the white light Li from the light source 10, the angle of incidence θ to the pattern TP, the design data regarding the pattern TP, and the refractive indexes of the layers constituting the pattern TP are input to the analytic order determination unit 32. The design data regarding the pattern TP includes the widths $W_{Si}$, $W_{Poly}$, and $W_{SiN}$ of the layers L1 to L3, the heights $H_{Si}$, $H_{Poly}$, and $H_{SiN}$, and the taper angle $\theta_T$ of the layer L1 that have been mentioned above. The process parameters needed for the determination of the shape model are also input to the layer stack model determination unit 34 via the unshown input unit.

Once the measurement starts, the analytic order determination unit 32 determines a priority order of analysis. Thus, the analytic order determination unit 32 calculates the feature value S that reflects the intensity of reflected light from each interface for each of the layers L1 to L3, and determines a priority order on the basis of the obtained feature value S. In the present embodiment, a priority order of analysis is determined in descending order of the feature values S.

The product of reflected light intensity and the shape parameter is used as the feature value S in the present embodiment. More specifically, the following expression is used:

$$S = W \times R_{Top} + H \times R_{Wall} \qquad \text{Expression (1)}$$

wherein W represents the width of the top surface of each layer, $R_{Top}$ represents the intensity of the reflected light from each top surface, H represents the height of each layer, and $R_{Wall}$ represents the intensity of the reflected light from the side surface of each layer.

The reflected light intensity can also be found from the reflectivity and transmittivity in each interface.

A method of calculating the feature value S is described in more detail. First, the method is described with reference to a drawing in which the pattern TP1 is more simplified for ease of description.

Figure 4:
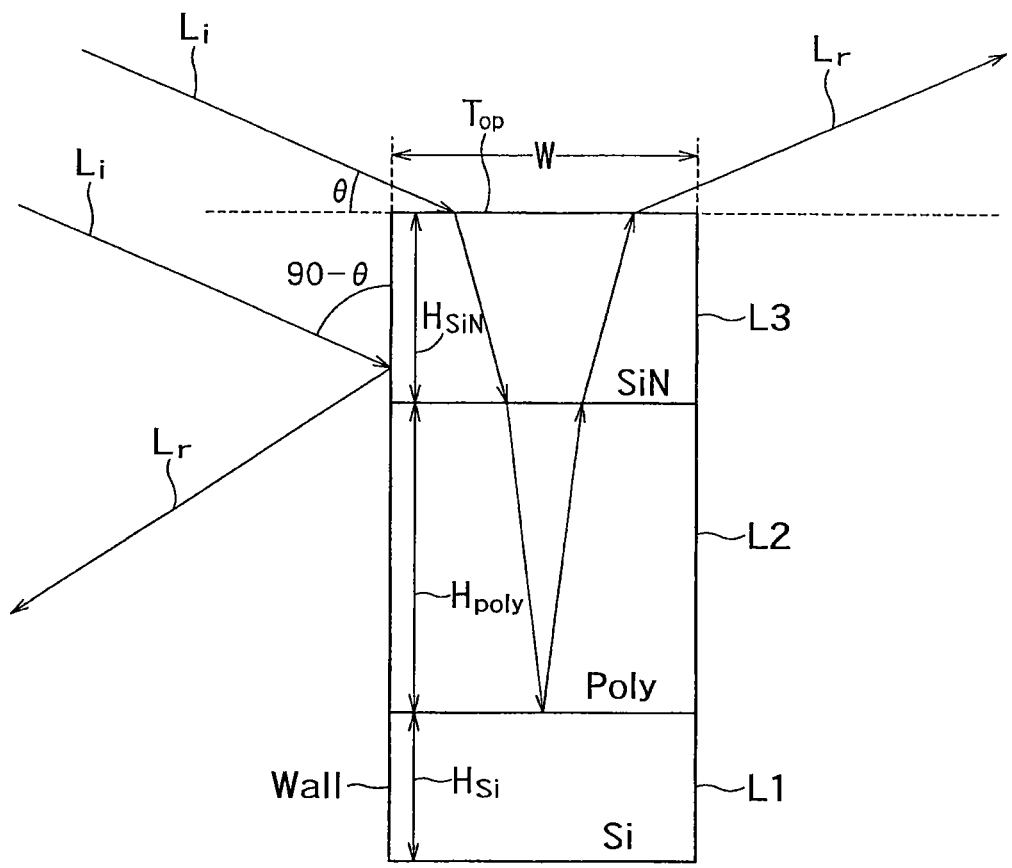
FIG. 4 is an example of a diagram in which the sectional shapes of layers of the pattern shown in FIG. 3 are rewritten to rectangular shapes.

FIG. 4 is an example of a diagram in which the sectional shapes of the layers L1 to L3 of the pattern TP1 shown in FIG. 3 are rewritten to rectangular shapes. Suppose that the white light Li enters the upper surface (top surface) (width W) of the rectangular pattern at the angle of incidence θ, and enters the side surface (Wall) at an angle of incidence (90°−θ).

Figure 5:
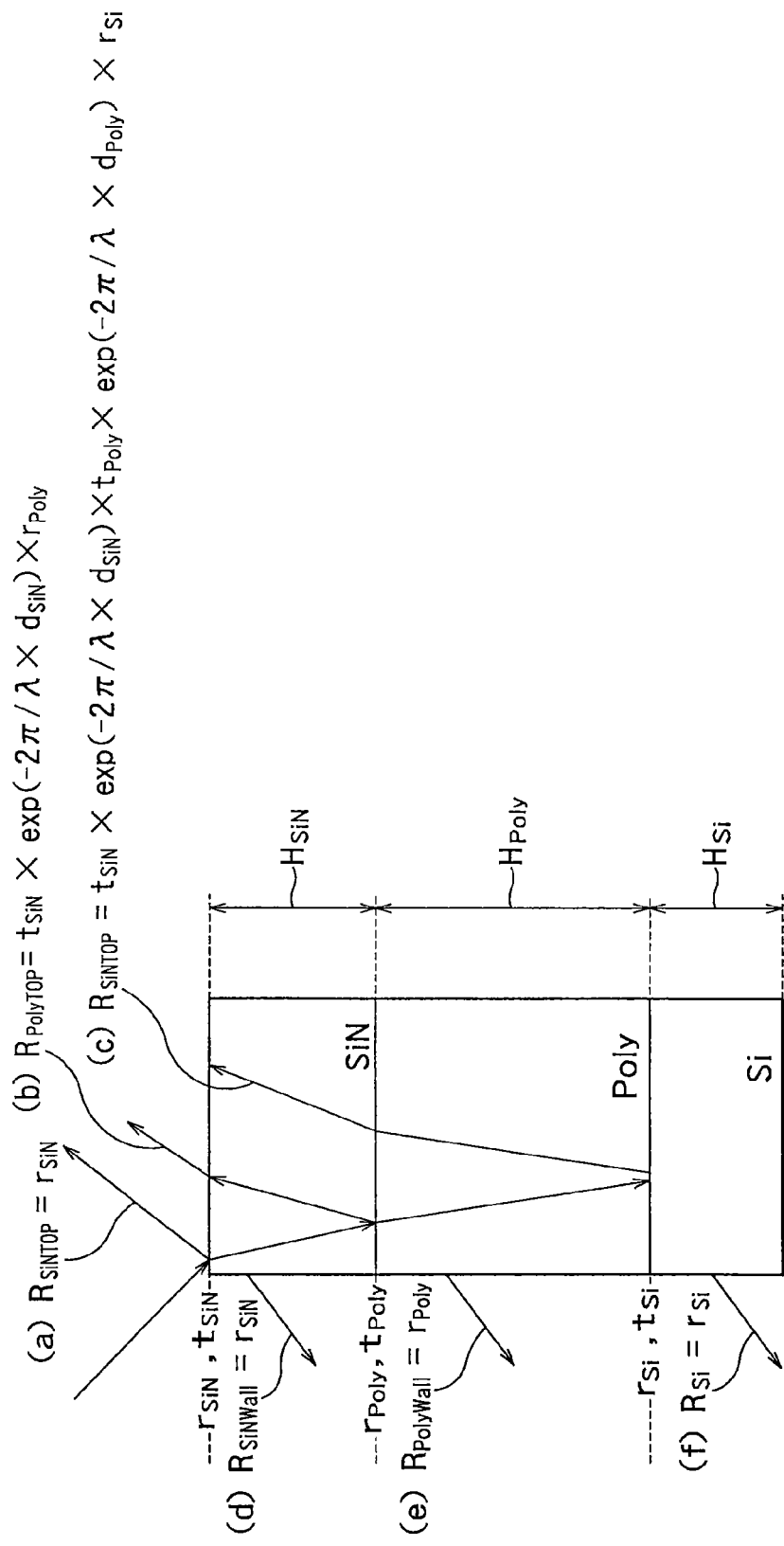
FIG. 5 is an example of a diagram illustrating reflected light generated from each interface of the pattern shown in FIG. 4.

The following reflected lights (a) to (f) are generated from the interfaces as shown in FIG. 5.

(a) Light $R_{SiNTop}$ exiting from the upper surface of the layer L3 (SiN)

(b) Light $R_{PolyTop}$ passing through the layer L3 (SiN), reflected at an interface (SiN/Poly) between the layer L3 (SiN) and the layer L2 (Poly), again passing through the layer L3 (SiN), and exiting from the upper surface of the layer L3 (SiN)

(c) Light $R_{SiTop}$ passing through the layer L3 (SiN) and the layer L2 (Poly), reflected at an interface (Poly/Si) between the layer L2 (Poly) and the layer L1 (Si), again passing through the layer L2 (Poly) and the layer L3 (SiN), and exiting from the upper surface of the layer L3 (SiN)

(d) Light $R_{SiNWall}$ reflected on the side surface of the layer L3 (SiN)

(e) Light $R_{PolyWall}$ reflected on the side surface of the layer L2 (Poly)

(f) Light $R_{SiWall}$ reflected on the side surface of the layer L1 (Si)

FIG. 6A shows an example of reflectivities and transmittivities of P-polarization and S-polarization found by the analytic order determination unit 32 for the lights generated from the upper surface (top surface) of the pattern TP1, that is, for (a) the light $R_{SiNTop}$, (b) the light $R_{PolyTop}$, and (c) the light $R_{SiTop}$ that have been mentioned above. The analytic order determination unit 32 uses the obtained values of the reflectivities and transmittivities to calculate the reflected light intensity $R_{Top}$ of the light generated from the upper surface (top surface) of each layer of the pattern TP1. In FIG. 6A, the value 20.0 which is an angle of light (top) associated with Air corresponds to the angle of incidence θ of the white light Li.

FIG. 6B shows an example of reflectivities of P-polarization and S-polarization found by the analytic order determination unit 32 for the lights generated from the side surface of the pattern TP1, that is, for (d) the light $R_{SiNWall}$, (e) the light $R_{PolyWall}$, and (f) the light $R_{SiWall}$ that have been mentioned above. The analytic order determination unit 32 uses the obtained values of the reflectivities to calculate the reflected light intensity $R_{Wall}$ of the light generated from the side surface of each layer of the pattern TP. In FIG. 6B, the value 70.0 which is an angle of light (wall) associated with Air corresponds to the angle of incidence (90°−θ) of the white light Li.

The analytic order determination unit 32 then calculates the feature value S represented by Expression (1) for each of the layers L1 to L3. That is, the following are found:

for the layer L3 (SiN):

$$S_{SiN} = W_{SiN} \times R_{SiNTop} + H_{SiN} \times R_{SiNWall},$$

for the layer L2 (Poly):

$$S_{Poly} = W_{Poly} \times R_{PolyTop} + H_{Poly} \times R_{PolyWall}, \text{ and}$$

for the layer L1 (Si):

$$S_{Si} = W_{Si} \times R_{SiTop} + H_{SiN} \times R_{SiWall}.$$

The analytic order determination unit 32 compares the calculated feature values $S_{SiN}$, $S_{Poly}$, and $S_{Si}$ of the layers, and determines a priority order of analysis from the comparison result. In the present embodiment, the analysis is prioritized in descending order of the feature values.

Figure 7:
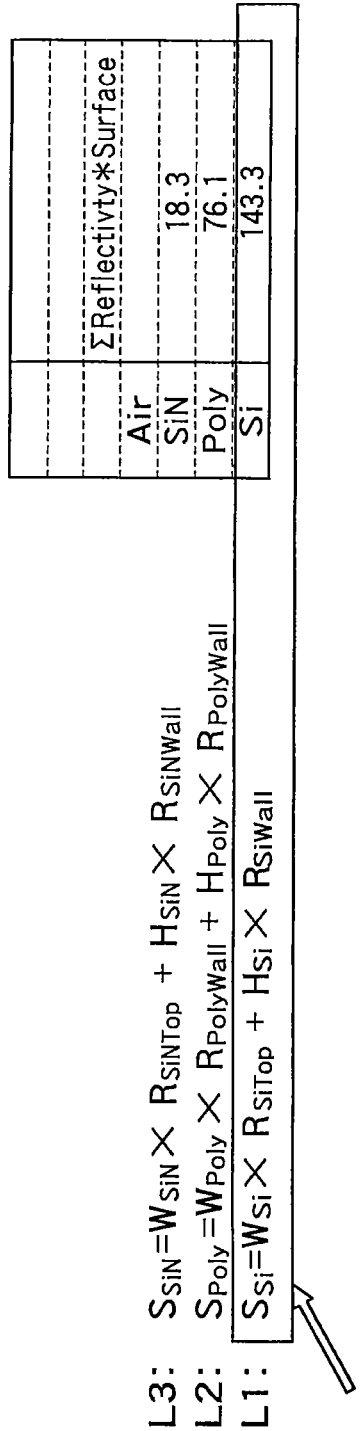
FIG. 7 is an example of a diagram showing calculation examples of feature amounts of the layers of the pattern shown in FIG. 4 together with computational expressions thereof.

FIG. 7 is a diagram showing calculation examples of the feature values $S_{SiN}$, $S_{Poly}$, and $S_{Si}$ of the layers L1 to L3 together with computational expressions thereof. In the example shown in FIG. 7, the feature value $S_{Si}$ is the highest, and the values $S_{Poly}$ and $S_{SiN}$ degrease in this order. Therefore, the analytic order determination unit 32 determines a priority order of the layers L1→L2→L3, and sends this information to the layer stack model determination unit 34.

The layer stack model determination unit 34 sequentially determines shape models of the layers in accordance with the priority order provided from the analytic order determination unit 32, and thereby determines a layer stack model of the pattern TP.

For example, if the priority order of the layers L1→L2→L3 is set as described above, shape parameters are first allocated in accordance with process variation expected from the process parameters for the layer L1 to generate a candidate model. In this case, design values are used as the shape parameters for the other layers L2 and L3 for convenience.

The layer stack model determination unit 34 then calculates a theoretical profile of the spectral profile by a simulation for each candidate model.

A referential pattern is then mounted on the stage S. This referential pattern is a pattern serving as a standard for library creation, and includes, for example, the pattern TP1 which is actually created on the wafer W and verified to be a conforming article.

If the white light Li is emitted by the light source 10 under the command of the computer 20 and enters the referential pattern, the detector 16 detects reflected light 15, and acquires an actual measured profile of the referential pattern and then sends the actual measured profile to the layer stack model determination unit 34.

The layer stack model determination unit 34 stores, in the storage device MR3, the actual measured profile of the referential pattern sent from the detector 16, performs fitting of the theoretical profile calculated by a simulation to this actual measured profile, and thereby specifies the most suitable candidate model and specifies this candidate model as the shape model of the layer L1.

The layer stack model determination unit 34 then allocates shape parameters regarding the layer L2 to generate a candidate model. In this case, design values are used as the shape parameters for the layer L3 for convenience.

Further, the layer stack model determination unit 34 calculates a theoretical profile of the spectral profile by a simulation for each candidate model. The layer stack model determination unit 34 then takes out the actual spectral profile of the pattern TP from the storage device MR3, performs fitting of the theoretical profile calculated by a simulation to the actual measured profile, and thereby specifies the most suitable candidate model and specifies this candidate model as the shape model of the layer L2.

The layer stack model determination unit 34 then specifies the shape model of the layer L3 by processing procedures substantially similar to those for the layers L1 and L2. In this case, the layer L3 is the last layer for which a shape model is to be specified, so that it is not necessary to use design data for the other layers for convenience in generating a candidate model.

Furthermore, the layer stack model determination unit 34 composes the shape models of the layers L1 to L3 that have been sequentially obtained by the processing procedures described above, and thereby determines a layer stack model of the pattern TP.

Finally, the layer stack model determination unit 34 matches the determined layer stack model to the theoretical profile to construct a library, and stores the library in the storage device MR3.

After the library is constructed in this manner, normal sectional shape measurement is conducted.

Specifically, the measurement target pattern TP is mounted on the stage S, and the white light Li is emitted by the light source 10 under the command of the computer 20 and enters the measurement target pattern TP. The detector 16 detects the reflected light Lr from the measurement target pattern TP, and acquires an actual measured profile and then sends the actual measured profile to the pattern sectional shape measurement unit 28.

The pattern sectional shape measurement unit 28 performs fitting of the theoretical profile in the library to the actual spectral profile sent from the detector 16 by referring to the library stored in the storage device MR3 via the control unit 22, and thus generates an optimum pattern sectional shape, and then measures the width, height, and taper angle of the pattern TP from the obtained sectional shape.

Figure 8A:
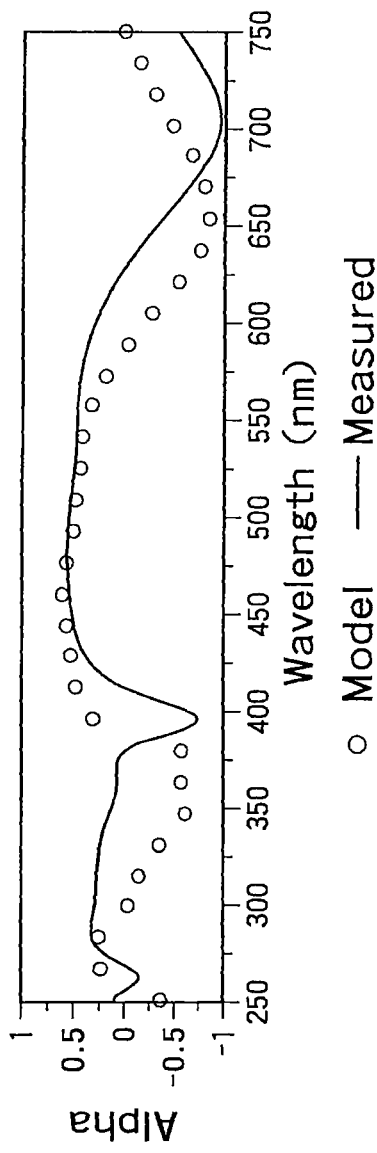
FIG. 8A is an example of a plotted graph showing an example of a theoretical profile obtained by existing software when a shape parameter is input at random, and an example of a measured profile obtained from a measurement target pattern.

FIG. 8A shows an example of a plotted graph showing an example of a theoretical profile obtained when nine variables of the widths, heights, and taper angles of the layers L1 to L3 are input to a simulator and automatically fitted by the use of existing software, and an example of a measured profile obtained from the measurement target pattern TP. In the example shown in FIG. 8A, there are parts in which the theoretical profile and the measured profile have considerably deviated from each other. Therefore, it is possible to measure values which are considerably different from the actual shape parameters may be obtained.

Figure 8B:
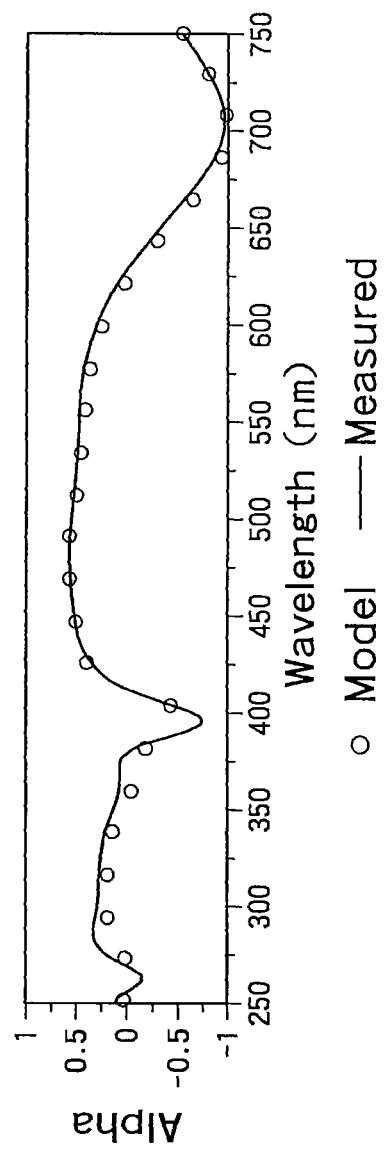
FIG. 8B is an example of a plotted graph showing an example of a theoretical profile in a library constructed by the measurement apparatus shown in FIG. 1, and an example of the measured profile obtained from the measurement target pattern.

FIG. 8B shows an example of a plotted graph showing an example of the theoretical profile in the library constructed according to the present embodiment, and an example of the measured profile obtained from the measurement target pattern TP. It is obvious that a theoretical profile close to the measured profile has been obtained compared to the theoretical profile in FIG. 8A.

Computational Expression (1) based on the product of the reflectivity and the shape parameter is used as the feature value S to determine a priority order of analysis in the above description, the feature value S is not exclusively found in this way. Any other indices that represent the degree of influence on the intensity of the spectral profile can be used.

For example, shape data may be allocated within a predetermined range regarding each of the layers L1 to L3 to calculate reflected light intensity, and the difference between a maximum value and a minimum value of the obtained reflected light intensity may be calculated as the feature value S.

A priority order can be determined by comparing $S_{SiN}$, $S_{Poly}$, and $S_{Si}$ that are obtained as above with one another. For example, in a manner similar to the case that uses Computational Expression (1) above, the analytic order determination unit 32 can prioritize the analysis in descending order of the feature values.

At least one measurement apparatus described above includes the analytic order determination unit 32 which calculates a feature value that reflects the intensity of reflected light from the interface for each of the layers constituting the measurement target pattern, and determines a priority order of analysis from the feature value S, so that a layer stack model in which the theoretical profile most approximates the measured profile can be uniquely found. Thus, an optimum library can be constructed regardless of the skill level of an operator. As a result, the pattern can be accurately measured.

(2) Measurement Method

The measurement method according to an embodiment is described with reference to FIG. 9 and FIG. 10.

(a) Embodiment 1

Figure 9:
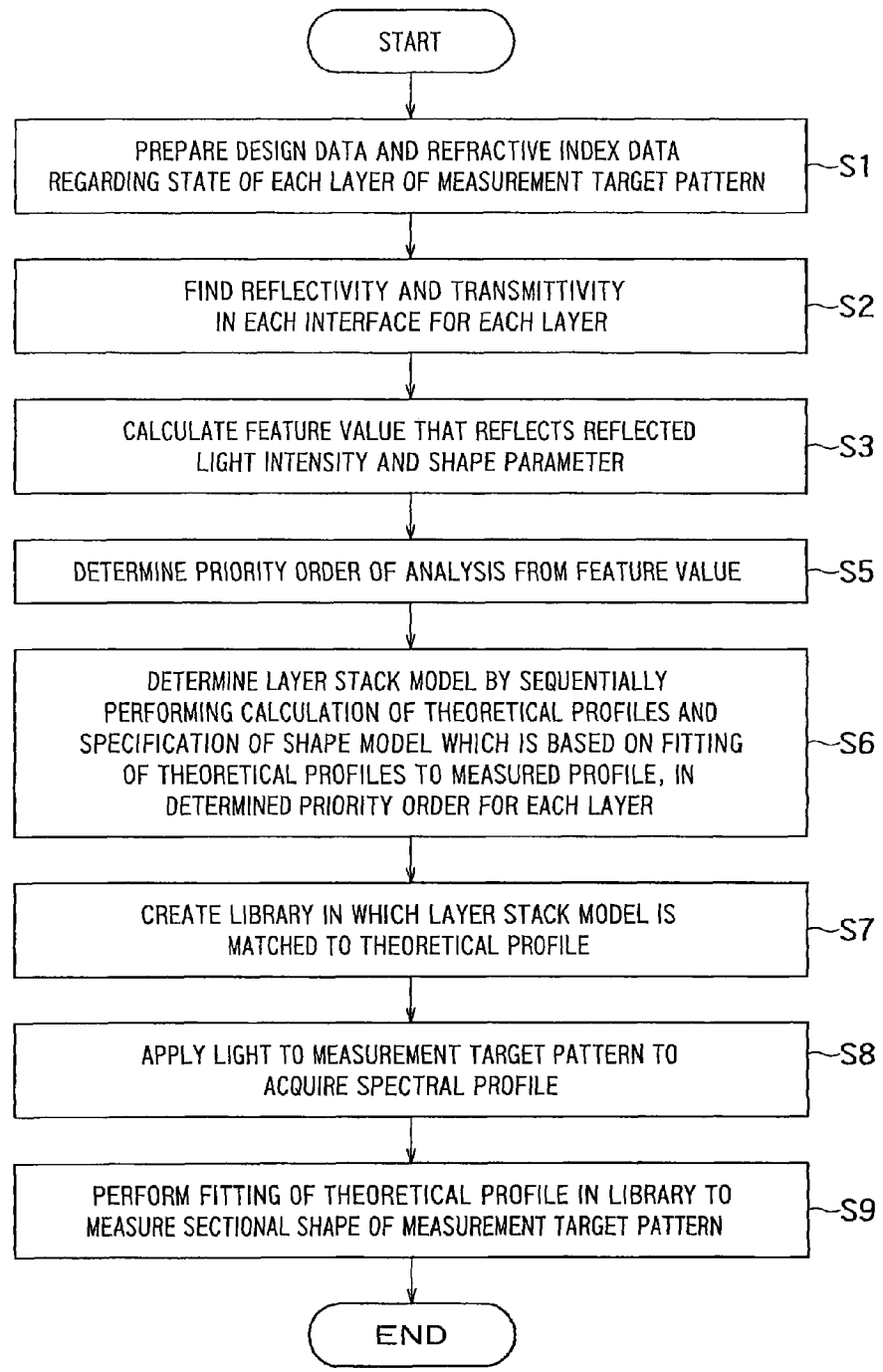
FIG. 9 is an example of a flowchart showing a general procedure of a measurement method according to Embodiment 1.

FIG. 9 is an example of a flowchart showing a general procedure of a measurement method according to Embodiment 1.

First, data necessary for measurement is prepared regarding a measurement target pattern (see FIG. 3) in which a plurality of layers are stacked. The necessary data includes design data and refractive index data regarding the shapes of the layers of the measurement target pattern (step S1). Other data include, for example, the wavelength λ of incident light (see Li in FIG. 1) and the angle of incidence (see θ in FIG. 1) to the measurement target pattern.

The reflectivity and transmittivity in each interface are calculated for each layer of the measurement target pattern (step S2).

The values of the obtained reflectivity and transmittivity are used to find reflected light intensity in each layer, and a feature value that reflects the obtained reflected light intensity and the shape pattern of each layer is calculated (step S3). A specific method of calculating the feature value is, for example, Expression (1) above.

A priority order of analysis for the layers constituting the measurement target pattern is then determined from the obtained feature value (step S5).

A layer stack model is then determined by sequentially performing the calculation of a plurality of theoretical profiles and the specification of a shape model in the determined priority order for each layer (step S6). The theoretical profiles can be calculated by an existing simulation. The shape model can be specified by applying light to a referential pattern serving as a standard for library creation and detecting reflected light to acquire an actual measured profile, and performing fitting of the theoretical profile to this measured profile. The referential pattern includes, for example, a measurement target pattern which is actually created on a wafer and verified to be a conforming article.

When the layer stack model is determined, a library can be created by matching the theoretical profile to the layer stack model (step S7).

Light is then applied to the measurement target pattern to acquire a spectral profile (step S8), and fitting of the theoretical profile in the created library is performed to the obtained measured profile to measure the sectional shape of the measurement target pattern (step S9).

(b) Embodiment 2

Figure 10:
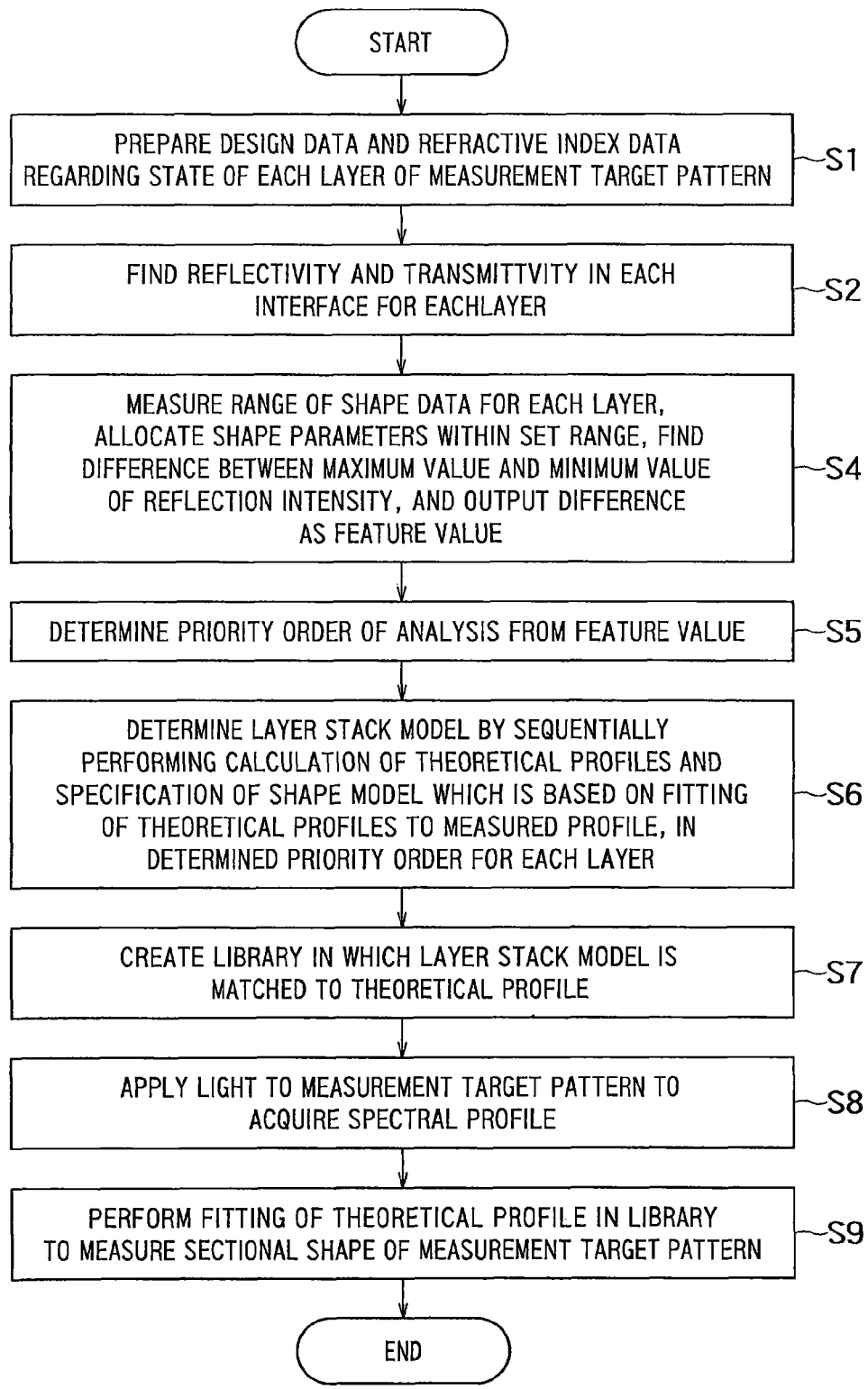
FIG. 10 is an example of a flowchart showing a general procedure of a measurement method according to Embodiment 2.

FIG. 10 is an example of a flowchart showing a general procedure of a measurement method according to Embodiment 2. As apparent from the contrast with FIG. 9, the measurement method according to the present embodiment is characterized in that the method of calculating a feature value to determine a priority order of analysis is different from that in Embodiment 1.

More specifically, the range of shape data is set for the layers constituting the measurement target pattern, shape parameters are allocated within the set range to calculate reflected light intensity, and a difference between a maximum value and a minimum value of the obtained reflected light intensity is found and output as the feature value of each layer (step S4).

According to this method, it is also possible to find a value that represents the degree of influence on the intensity of the spectral profile.

The procedures in the measurement method according to the present embodiment are substantially the same as the above-described procedures in Embodiment 1 except for step S4. Therefore, repeated explanations are omitted.

At least one measurement method described above includes the procedure of calculating a feature value that reflects the intensity of reflected light from the interface for each of the layers constituting the measurement target pattern, and determining a priority order of analysis from the feature value, so that a layer stack model in which the theoretical profile most approximates the measured profile can be uniquely found. Thus, an optimum library can be constructed regardless of the skill level of an operator. As a result, the pattern can be accurately measured.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A measurement apparatus comprising:
a library creation processor programmed to create a library in which a layer stack model is matched to a theoretical profile regarding a pattern constituted by a plurality of stacked layers, the theoretical profile being obtained by calculating a spectral profile expected when light is applied to the layer stack model;
a detector configured to output an actual measured profile acquired by applying light to a measurement target pattern obtained when the pattern is actually created; and
a measurement processor programmed to measure the sectional shape of the measurement target pattern by performing fitting of the theoretical profile in the library to the actual measured profile,
wherein the library creation processor creates the layer stack model by calculating a feature value that reflects the intensity of reflected light from an interface for each of the layers, determining a priority order of analysis from the feature value of the plurality of stacked layers, and sequentially performing fitting of the theoretical profile to the measured profile in the determined priority order.

2. The apparatus of claim 1,
wherein the feature value is represented by the following expression:

$$S = W \times R_{Top} + H \times R_{Wall}$$

in which S is the feature value, W is the width of the top surface of each layer, $R_{Top}$ is the intensity of reflected light from the top surface, H is the height of each layer, and $R_{Wall}$ is the intensity of reflected from the side surface of each layer.

3. The apparatus of claim 1,
wherein the library creation processor allocates shape data within a predetermined range for each layer to calculate reflected light intensity, and calculates the difference between a maximum value and a minimum value of the obtained reflected light intensity as the feature value.

4. A measurement method comprising:
creating a library in which a layer stack model is matched to a theoretical profile regarding a pattern constituted by a plurality of stacked layers, the theoretical profile being obtained by calculating a spectral profile expected when light is applied to the layer stack model;
acquiring an actual measured profile by applying light to a measurement target pattern obtained when the pattern is actually created; and
measuring the sectional shape of the measurement target pattern by performing fitting of the theoretical profile in the library to the actual measured profile,
wherein the layer stack model is created by calculating a feature value that reflects the intensity of reflected light from an interface for each of the layers, determining a priority order of analysis from the feature value of the plurality of stacked layers, and sequentially performing fitting of the theoretical profile to the measured profile in the determined priority order for all the layers constituting the pattern.

5. The method of claim 4,
wherein the feature value is represented by the following expression:

$$S = W \times R_{Top} + H \times R_{Wall}$$

in which S is the feature value, W is the width of the top surface of each layer, $R_{Top}$ is the intensity of reflected light from the top surface, H is the height of each layer, and $R_{Wall}$ is the intensity of reflected light from the side surface of each layer.

6. The method of claim 4, wherein the feature value is the difference between a maximum value and a minimum value of reflected light intensity calculated by allocating shape data within a predetermined range for each layer.

* * * * *